United States Patent
Takahara et al.

(10) Patent No.: US 6,504,156 B1
(45) Date of Patent: Jan. 7, 2003

(54) CERAMIC SCINTILLATOR MATERIAL AND MANUFACTURING METHOD THEREOF, AND RADIATION DETECTOR THEREWITH AND RADIATION INSPECTION APPARATUS THEREWITH

(75) Inventors: Takeshi Takahara, Yokohama (JP); Akihisa Saito, Kamakura (JP); Yukihiro Fukuta, Yokohama (JP); Eiji Oyaizu, Yokohama (JP); Masaaki Tamatani, Fujisawa (JP)

(73) Assignee: Kabushiki Kaisha Toshiba, Kawasaki (JP)

(*) Notice: Subject to any disclaimer, the term of this patent is extended or adjusted under 35 U.S.C. 154(b) by 84 days.

(21) Appl. No.: 09/615,057

(22) Filed: Jul. 12, 2000

(30) Foreign Application Priority Data

Jul. 16, 1999 (JP) ............................................ 11-203774

(51) Int. Cl.[7] ................................................. G01T 1/20
(52) U.S. Cl. ................................................. 250/361 R
(58) Field of Search ............................ 250/361 R, 367; 378/21, 51; 252/301.45; 264/125

(56) References Cited

U.S. PATENT DOCUMENTS

| 4,525,628 A | 6/1985 | Dibianca et al. ............ 250/367 |
| 4,733,088 A | 3/1988 | Yamada et al. ............. 250/483.1 |
| 5,296,163 A | * 3/1994 | Leppert et al. ......... 252/301.4 S |
| 5,609,793 A | 3/1997 | Yokota et al. .......... 252/301.4 S |
| 6,245,184 B1 | * 6/2001 | Riedner et al. ........ 250/361 R X |

FOREIGN PATENT DOCUMENTS

| JP | 59-027283 | 2/1984 |
| JP | 59-045022 | 11/1984 |
| JP | 5-016756 | 3/1993 |
| JP | 58-204088 | 11/1993 |
| JP | 7-188655 | 7/1995 |

* cited by examiner

*Primary Examiner*—Constantine Hannaher
*Assistant Examiner*—Shun Lee
(74) *Attorney, Agent, or Firm*—Foley & Lardner

(57) ABSTRACT

A ceramic scintillator material consists of a sintered body of a rare earth oxysulfide phosphor containing Pr as an activator. The sintered body has a texture where coarse grains of irregular polyhedron and slender fine grains are intermixed. The coarse grains have a shape of for instance a dimension (average value) in the range of 50 to 100 $\mu$m, the fine grains having a shape of which average short axis is in the range of 2 to 5 $\mu$m and average long axis in the range of 5 to 100 $\mu$m. An area ratio of the coarse grains to the fine grains is in the range of 10:90 to 60:40. Such a ceramic scintillator material has, in addition to excellent light output (high sensitivity), mechanical strength capable of coping with downsizing of a detector. Furthermore, non-uniformity in sensitivity that causes artifacts can be decreased.

17 Claims, 5 Drawing Sheets

FIG. IA
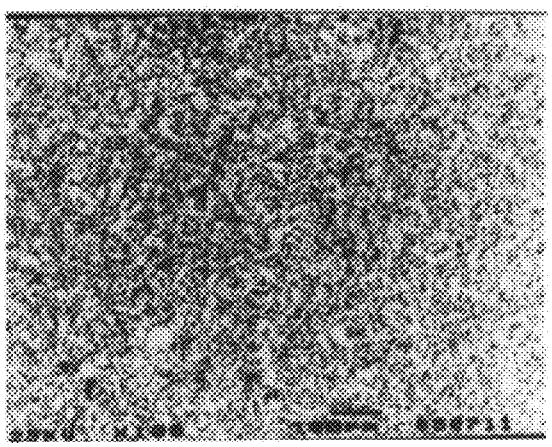
100μm
FIG. IB
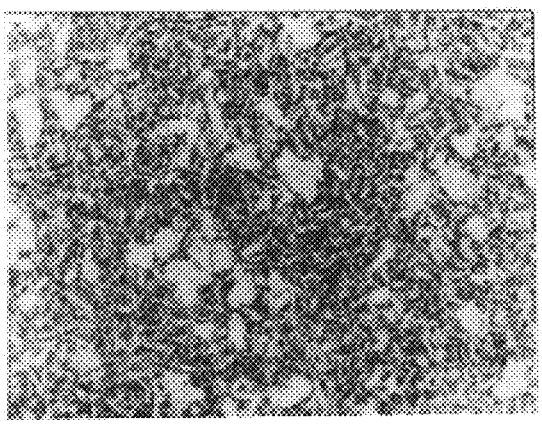
100μm
FIG. IC
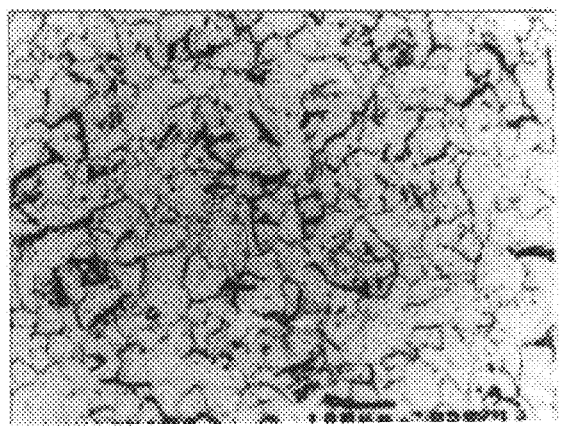
100μm

CERAMIC SCINTILLATOR MATERIAL AND MANUFACTURING METHOD THEREOF, AND RADIATION DETECTOR THEREWITH AND RADIATION INSPECTION APPARATUS THEREWITH

BACKGROUND OF THE INVENTION

1. Field of the Invention

The present invention relates to ceramic scintillator material converting radiation such as X-rays into visible light and a manufacturing method thereof, and a radiation detector therewith and a radiation inspection apparatus therewith.

2. Description of the Related Art

In the field of medical diagnosis and industrial nondestructive inspection, inspections using a radiation inspection apparatus such as an X-ray computed tomography apparatus (hereinafter referred to as X-CT apparatus) are in practice. An X-CT apparatus is constituted of an X-ray tube (X-ray source) emitting a fan-shaped X-ray beam and an X-ray detector in which plural X-ray detecting elements are arranged, both of which being disposed facing to each other with a sectional plane of an object as a center. In the X-CT apparatus, while circulating an X-ray tube with respect to an object, a fan-shaped X-ray beam from an X-ray tube is illuminated on the object, X-rays transmitted through the object being detected by the X-ray detector to obtain X-ray absorption data. Thereafter, a computer analyzes the X-ray absorption data to reconstruct a tomogram.

For a radiation detector of the aforementioned X-CT apparatus, detector elements such as solid state scintillator are widely in use. In the radiation detector using the solid state scintillator, due to easiness in downsizing the detector element to increase number of channels, resolution of the X-CT apparatus can be readily improved.

The scintillator, when excited by radiation such as X-rays, emits electromagnetic waves in the wavelengths of visible light or near visible light. As solid-state materials having such scintillation characteristics, single crystals such as NaI, CsI and $CdWO_4$, polycrystalline materials (ceramics) such as BaFCl: Eu, LaOBr: Tb, CsI: Tl, $CaWO_4$ and $CdWO_4$ (cf. Japanese Patent Publication (KOKOKU) No. SHO 59-45022 and so on official gazette), polycrystalline materials (ceramics) of rare earth oxides having cubic crystal structure such as $(Gd, Y)_2O_3$:Eu (cf. Japanese Patent Laid-open Application (KOKAI) No. SHO 59-27283 official gazette and so on) and polycrystalline materials (ceramics) of rare earth oxysulfide such as $Gd_2O_2S$:Pr (cf. Japanese Patent Laid-open Application (KOKAI) No. SHO 58-204088 official gazette and so on) are known.

Among various kinds of solid-state scintillators such as mentioned above, ceramics of rare earth oxysulfide phosphors in particular, being high in emission efficiency, are suitable for scintillators. Accordingly, a combination of a rare earth oxysulfide ceramic scintillator and a photodiode is coming into wide use as a radiation detector.

The ceramic scintillator materials (phosphor ceramics) like this can be obtained by molding rare earth oxysulfide powder into an appropriate shape, followed by sintering. From the obtained sintered body, planar slabs in disk plate shape or rectangular plate shape are cut out, first. Next, scintillator chips of rectangular bar are cut out from the slabs, followed by slicing each of these scintillator chips into a plurality of segments. A detector element is constituted of a scintillator block in which for instance plural segments are integrated.

Now, as to rare earth oxysulfide phosphor ceramics, in order to improve transparency (light transmittance), sintering properties or the like, various kinds of inventions have been proposed. For instance, Japanese Patent Laid-open Application (KOKAI) No. HEI 7-188655 official gazette discloses that, by reducing contents of impurities in the phosphor ceramics such as $Gd_2O_2S$:Pr or the like, in particular by reducing a content of phosphate group $(PO_4)$ therein down to 100 ppm or less, light output of the scintillator can be improved.

Further, in Japanese Patent Publication (KOKOKU) No. HEI 5-16756 official gazette, rare earth oxysulfide powder is mixed with fluorides such as LiF, $Li_2GeF_6$ and $NaBF_4$ as sintering aide, followed by sintering the mixture with a hot isostatic press (HIP), thereby obtaining highly densified phosphor ceramics. Here, through densification of the phosphor ceramics, light output of the scintillator is improved.

As mentioned above, as to the transparency and sintering properties of the rare earth oxysulfide phosphor ceramics, so far there have been various kinds of proposals. However, in a recent X-CT apparatus, downsizing of the detector elements is demanded due to higher resolution (multi-channel), and downsizing/lengthening of the detector elements is further demanded due to multi-section tomography. Due to these, new problems are occurring.

That is, due to the tendency of downsizing of the detector element, it becomes necessary to process the phosphor ceramics obtained through the sintering step into scintillator chips of a size of for instance such as a width of 1 mm or less, a length of 20 to 40 mm and a depth of 2 to 3 mm. The scintillator chips of such a size, due to the phosphor ceramics being the polycrystalline body, are liable to cause breaking and chipping during processing and assembling the detectors. Thereby, yield of the ceramic scintillators is deteriorated.

For such points, as described in for instance Japanese Patent Publication (KOKOKU) No. HEI 5-16756 official gazette, densification of the phosphor ceramics is to a certain degree effective. However, in the phosphor ceramics disclosed in the foregoing official gazette, due to the addition of a fluoride as a sintering aide, the sintering aide remains as impurities in the phosphor ceramics to result in deterioration of emission characteristics. This lowers the sensitivity of the ceramic scintillator. Further, in the above official gazette, due to the activity of the sintering aide, part of grains grows in pillar. However, in the phosphor ceramics having such a sintered texture, due to the smaller grain size of other than pillar-shaped grains, sufficient strength can not be obtained. In addition, the light output (sensitivity) also is disadvantageous.

Further, in a trend toward higher resolution of the X-CT apparatus, if artifacts (pseudo-image) would appear when reconstructing a sectional image through computer processing of the X-ray intensities after transmission of an object, this would cause severe problems. The artifact is often caused by local nonuniformity of the sensitivity of the ceramic scintillators. Since appearing of the artifacts is detrimental to medical diagnosis and nondestructive inspection, the ceramic scintillators are demanded to have further uniform sensitivity distribution to cope with the trend toward higher resolution of the CT apparatus.

In making the sensitivity of the ceramic scintillator uniform, in addition to making the properties of each scintillator chip uniform, it is effective to constitute one channel with the plural segments cut out of one scintillator chip. However, the existing phosphor ceramics are liable to break and tip when processing into chips. Accordingly, there is a limit in the length of one scintillator chip. That is, though a longer scintillator chip is demanded, there is a limit in lengthening the existing scintillator chip.

In particular, in the X-CT apparatus for multi-section tomography, one channel is constituted of plural segments. Accordingly, number of segments sliced out of one scintillator chip is necessary to be increased. However, since the scintillator chip cut out of the existing phosphor ceramics can not cope with such a demand, one channel is constituted of segments sliced out of a plurality of scintillator chips.

SUMMARY OF THE INVENTION

Accordingly, an object of the present invention is to provide a ceramic scintillator material that, while maintaining excellent light output, has sufficient mechanical strength capable of coping with downsizing of a detector, and a method for manufacturing thereof. In more specific, the present object is to provide a ceramic scintillator material having mechanical strength capable of putting a long length scintillator chip to practical use. Another object of the present invention is to provide a ceramic scintillator material in which sensitivity nonuniformity that causes artifacts is decreased and a method for manufacturing thereof. Still another object of the present invention is, by using such ceramic scintillator material to improve resolution and image accuracy, to provide a radiation detector and a radiation inspection apparatus in which medical diagnosis ability and nondestructive inspection precision are improved.

The present inventors variously studied the relationship between sintered texture of rare earth oxysulfide phosphor ceramics and sensitivity and mechanical strength thereof. As a result, the inventors found that in phosphor ceramics of which sensitivity is improved due to purification of phosphor raw materials, by intermixing grains of relatively large irregular polyhedron (hereinafter referred to as coarse grains) and relatively small slender grains (hereinafter, referred to as fine grains) to form a sintered texture, in addition to improving the strength, the sensitivity can be further improved. Further, due to the superiority in the uniformity of the sensitivity of the phosphor ceramics that have the aforementioned intermixed texture, the artifacts can be effectively suppressed from occurring.

The present invention is based on the above mentioned findings. That is, a ceramic scintillator material of the present invention is a ceramic scintillator material comprising a sintered body of a rare earth oxysulfide phosphor that contains praseodymium as a primary activator, the sintered body having a texture in which coarse grains of irregular polyhedron and slender fine grains are intermixed.

In the ceramic scintillator material of the present invention, the coarse grains constituting a sintered body texture are preferable to have an average grain size in the range of 50 to 100 μm, the slender fine grains being preferable to have an average short axis in the range of 2 to 5 μm and an average long axis in the range of 5 to 100 μm. Further, a ratio in a cross section of the sintered body of an area ($S_1$) which the coarse grains occupy to an area ($S_2$) which the fine grains occupy is preferable to be in the range of $S_1:S_2=10:90-60:40$.

The ceramic scintillator material of the present invention can have various shapes according to use mode or use step. As the specific shapes of the ceramic scintillator material, planar scintillator slab and rectangular rod of scintillator chip can be cited. Due to the higher strength of the present ceramic scintillator material, for the scintillator slab, a disc of a diameter of 20 mm or more and a thickness of 0.5 mm or more, or a rectangular plate of a length of a short side of 20 mm or more, that of a long side of 110 to 500 mm and a thickness of 0.5 mm or more can be materialized. For the scintillator chip, a shape of a length of 20 mm or more, a width of 0.5 to 2 mm and a thickness of 0.5 to 3 mm can be materialized.

A method for manufacturing the present ceramic scintillator is one of manufacturing a ceramic scintillator material comprising a sintered body of a rare earth oxysulfide phosphor containing praseodymium as a primary activator. Here, heat treatment conditions and/or pressurizing conditions during manufacturing the sintered body are characterized in being controlled so that the texture of the sintered body becomes one in which the coarse grains of irregular polyhedrons and slender fine grains are intermixed. As concrete conditions, for instance conditions of HIP process can be cited.

A radiation detector of the present invention comprising the present ceramic scintillator material comprises means for generating luminescence from the ceramic scintillator material according to incident radiation and photoelectric conversion means for receiving the generated luminescence from the luminescence generating means to convert the light output into an electrical output.

A radiation detector of the present invention is effective particularly in a structure in which the luminescence generating means comprise a plurality of channels. In this case, the respective channels in the luminescence generating means are constituted of plural segments manufactured by slicing a scintillator chip of rectangular rod consisting of the present scintillator material which are integrated in a direction approximately orthogonal to a direction of arrangement of plural channels.

A radiation inspection apparatus of the present invention comprises a radiation source emitting radiation to an object and the present radiation detector detecting radiation transmitted through the object. The present radiation inspection apparatus is effective in an X-CT apparatus of higher resolution and higher precision, contributing further in putting an X-CT apparatus of multi-section tomography into practical use.

BRIEF DESCRIPTION OF THE DRAWINGS

FIG. 1A, FIG. 1B and FIG. 1C are photographs showing in enlargement sections of textures of sintered bodies that show growth steps of grains of the sintered body constituting a ceramic scintillator material, FIG. 1A being a sectional photograph showing in enlargement a sintered texture consisting of agglomerates of fine grains, FIG. 1B being a sectional photograph showing in enlargement a sintered texture consisting of the present ceramic scintillator material, FIG. 1C being a sectional photograph showing in enlargement a sintered texture consisting of agglomerates of coarse grains of irregular polyhedrons.

DESCRIPTION OF THE PREFERRED EMBODIMENTS

Figure 2:
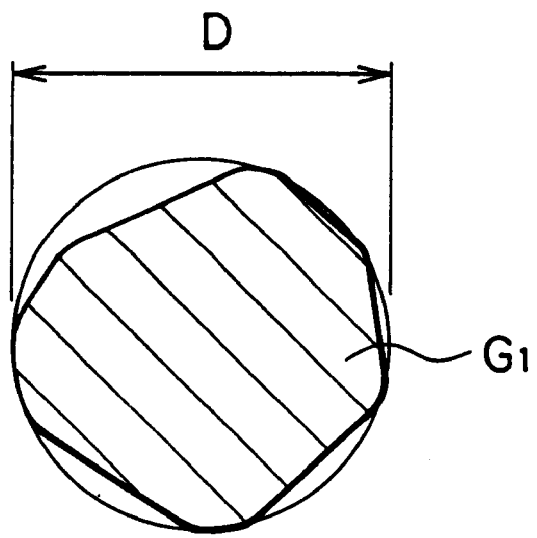
FIG. 2 is a diagram for explaining a size of a coarse grain of irregular polyhedron.

In the following, modes for implementing the present invention will be explained.

A ceramic scintillator material of the present invention is composed of a sintered body (phosphor ceramics) of a rare earth oxysulfide phosphor containing praseodymium (Pr) as an activator. As the rare earth oxysulfide phosphor, for instance oxysulfides of rare earth elements such as yttrium (Y), gadolinium (Gd), lanthanum (La) and lutetium (Lu) can be cited.

In the present ceramic scintillator material, it is preferable to use a phosphor material having a composition substantially expressed by General formula:

$$RE_2O_2S:Pr \qquad (1)$$

(in the formula, RE denotes at least one kind of element selected from Y, Gd, La and Lu).

Among the aforementioned rare earth elements, Gd is particularly large in X-ray absorption coefficient, contributing in an improvement of light output of the phosphor ceramics. Accordingly, in the present invention, it is preferable to use $Gd_2O_2S:Pr$ phosphor. Part of Gd can be replaced by the other rare earth elements. In this case, an amount of replacement by the other rare earth elements is preferable to be 10 mol % or less.

That is, in the present ceramic scintillator material, in particular, phosphor material substantially expressed by the following formula is preferable.

General formula:

$$(Gd_{1-x}, RE'_x)_2O_2S:Pr \qquad (2)$$

(in the formula, RE' denotes at least one kind of element selected from Y, La and Lu, x being number satisfying $0 \leq x \leq 0.1$).

In the present invention, as an activator effective in obtaining high light output from the rare earth oxysulfide phosphor, praseodymium (Pr) is used. The Pr, compared with the other activators, can reduce an amount of afterglow. Accordingly, the rare earth oxysulfide phosphor containing Pr as an activator is effective as luminescence generating means of a radiation detector.

The content of Pr is preferable to be set in the range of 0.001 to 10 mol % relative to a phosphor host (for instance $Gd_2O_2S$). When the content of Pr exceeds 10 mol %, the light output decreases. By contrast, when the content of Pr is less than 0.001 mol %, Pr can not sufficiently function as the primary activator. Accordingly, Pr is more preferably contained in the range of 0.01 to 1 mol %.

In the present invention, in addition to the Pr as the primary activator, a slight amount of at least one kind selected from Ce, Zr and P can be contained as a coactivator in the rare earth oxysulfide phosphor. These respective elements are effective in suppressing sensitivity deterioration caused by long-term X-ray irradiation, afterglow or the like. Total content of these coactivators is preferable to be set in the range of 0.00001 to 0.1 mol % with respect to the phosphor host.

Further, a sintered body constituting the present ceramic scintillator material is preferable to consist of a high purity phosphor material. An impurity, being a cause of deteriorating sensitivity of a scintillator, is preferable to be reduced as far as possible. In particular, phosphate group ($PO_4$), being a cause of deteriorating sensitivity, is preferable to be contained 150 ppm or less. Further, as disclosed in Japanese Patent Publication (KOKOKU) No. HEI 5-16756 official gazette, when high densification is attained due to the use of the sintering aide such as fluorides, as mentioned above, the sintering aide remains as impurity to result in causing deterioration of the sensitivity under long-term X-ray irradiation.

The present ceramic scintillator material is composed of a sintered body of the aforementioned rare earth oxysulfide phosphor. When a cross section thereof is observed, coarse grains of relatively large irregular polyhedron and relatively small and long fine grains are found intermixed to form a sintered texture.

High purity rare earth oxysulfide phosphor powder is molded into an appropriate shape by use of a cold isostatic press, the molded body is encapsulated in a metal capsule and sealed, followed by hot isostatic pressing (HIP) under high temperature and high pressure conditions to sinter. As the HIP sintering goes on, grains grow according to the growth steps such as shown in the following. The growth steps of the grains of the rare earth oxysulfide phosphor sintered body will be explained with reference to enlarged sectional photographs of the sintered body shown in FIG. 1A, FIG. 1B and FIG. 1G.

That is, as the HIP sintering proceeds, as shown in FIG. 1A, first sintered agglomerates of primary particles of phosphor are observed. Then, as shown in FIG. 1B, a texture in which slender rod shaped grains of relatively small grain size and relatively large grains of irregular polyhedron are intermixed is observed. When the HIP sintering further proceeding, as shown in FIG. 1C, the sintered body as a whole grows into coarse grains of irregular polyhedron.

Of each of the sintered textures of the aforementioned rare earth oxysulfide phosphor, bending strength, sensitivity and sensitivity distribution are measured. It is found that when, as shown in FIG. 1B, the coarse grains of irregular polyhedron and slender fine grains are intermixed to form a texture, high mechanical strength is shown and sensitivity and uniformity thereof are excellent. The relationship between the aforementioned growth steps of the grains of a rare earth oxysulfide phosphor and the strength and sensitivity characteristics based thereon is for the first time found through the present inventor's observation of grain structures appearing on the section and measurement of the bending strength and sensitivity and sensitivity distribution of many samples manufactured by varying HIP conditions.

According to the commonsense of the existing ceramic technology, in view of optical properties and uniformity of mechanical strength, the phosphor ceramics having a uniform grain structure such as shown in FIG. 1C have been considered to have excellent characteristics. However, the present inventors found from many experimental results as shown in FIG. 1B that, when a sintered body has an intermixed texture of the coarse grains of irregular polyhedron and slender fine grains, the scintillator material excellent in the strength, the sensitivity and uniformity of the sensitivity distribution can be obtained. That is, a sintered body that has the intermixed texture shows optimum characteristics as scintillator material.

The sintered texture such as shown in FIG. 1B, based on Of each of the sintered textures of the aforementioned the intermixing of the coarse grains of irregular polyhedron and the slender fine grains, largely contributes in an improvement of mechanical strength of the ceramic scintillator material. By making the ceramic scintillator material (sintered body) much stronger, in processing in a shape of for instance such as a length of 20 mm or more, a width of 0.5 mm or more, and a thickness of 0.5 mm or more, the ceramic scintillator material can be largely suppressed from being broken and chipped. Similarly, also in mounting a scintillator chip in a detector, the scintillator chip can be suppressed from being broken and chipped.

Further, in the sintered body having an intermixed texture such as shown in FIG. 1B, due to a strain releasing action of the fine grains that exist surrounding the coarse grains, the sensitivity of the ceramic scintillator material can be further improved. In addition, due to the excellence of the uniformity of the sensitivity distribution, the artifacts or the like can be effectively suppressed from occurring. These largely contribute in materializing the downsizing and higher resolution of a radiation detector.

On the other hand, when a sintered texture due to the HIP process is one such as shown in FIG. 1A, due to smaller grain size, light emitted under X-ray irradiation experiences a multiple scattering within the sintered body, resulting in a less amount of the emission drawn outside the sintered body. Accordingly, the sensitivity becomes smaller. Further, since phosphor particles bind each other less strongly to make the sintered body itself brittle, the sintered body may be much broken and chipped during processing the sintered body and assembling a detector.

When, as shown in FIG. 1C, a sintered body as a whole grows into grains of random and irregular polyhedron, the strength becomes lower than that of the intermixed texture shown in FIG. 1B. Further, due to an increase of strain in the grains, the sensitivity decreases. In addition to the above, the sensitivity distribution width also becomes larger. As a result, when such the phosphor ceramics (scintillator material) are applied to a radiation detector, the artifacts are likely to appear.

A phenomenon that in the growth process of grains the slender grains such as shown in FIG. 1B appear is characteristic to rare earth oxysulfide phosphors such as $Gd_2O_2S$ phosphor. Though the mechanism of the growth of the slender grains is not sufficiently elucidated, it is assumed that anisotropic hexagonal crystal structure of the rare earth oxysulfide phosphor causes this.

In the fine texture of the present ceramic scintillator material, the coarse grains of irregular polyhedron are preferable to have a shape of which average grain size is in the range of 50 to 100 $\mu$m. On the other hand, the slender fine particles are preferable to have a shape of which average short axis is in the range of 2 to 5 $\mu$m and average long axis in the range of 5 to 100 $\mu$m. When the coarse grains of irregular polyhedron and the slender fine grains have such shapes, the strength, sensitivity and uniformity of the sensitivity distribution can be improved with further reproducibility.

Figure 3:
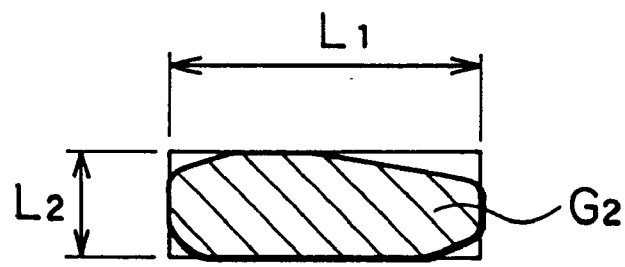
FIG. 3 is a diagram for explaining a short axis and a long axis of a slender fine grain.

Here, as shown in FIG. 2, a size of a coarse grain $G_1$ of irregular polyhedron denotes a diameter D of a smallest circle completely circumscribing it. In addition, as shown in FIG. 3, a long axis and short axis of a slender fine grain $G_2$ are defined as follows. That is, when circumscribing the fine grain $G_2$ with two pairs of straight lines, a length of a long side $L_1$ and a length of a short side $L_2$ of a circumscribing rectangle formed of these straight lines denote the long axis and short axis, respectively.

In a cross section of a sintered body, a ratio of an area ($S_1$) which the coarse grains occupy to that ($S_2$) which fine grains occupy is preferable for the ratio $S_1:S_2$ to be in the range of 10:90 to 60:40. When the ratio of the area $S_1$ that the coarse grains occupy is less than 10%, the light output (sensitivity) is liable to be caused low. By contrast, when the ratio of the area $S_1$ that the coarse grains occupy exceeds 60%, the strength may not be sufficiently improved and the sensitivity tends to show fluctuation. Accordingly, the aforementioned area ratio $S_1:S_2$ is further preferable to be in the range of 20:80 to 50:50.

Here, in the present invention, average shapes of the coarse grains and fine grains are measured in the following way. That is, first, a surface of a sintered body is mirror polished, followed by etching with an etching solution of a composition of hydrochloric acid:water:hydrogen peroxide =1:1:1. After drying, an arbitrary surface thereof is observed with a scanning electron microscope (SEM). Among enlarged photographs showing grains, first, with that of magnification rate of 100 times, the coarse grains and fine grains are classified. Then, arbitrary grains are selected to observe under high magnification rates of for instance 350, 750 and measured of shapes of the respective grains. The shapes of the respective grains are shown in FIGS. 2 and 3. More than 10 pieces of the grains of each type are observed to obtain average values. These values show average shapes of the coarse grains and fine grains.

Similarly, the ratio of the area ($S_1$) that the coarse grains occupy to the area ($S_2$) that the fine grains occupy is obtained from the following. That is, the area that the coarse grains occupy in the enlarged photograph (SEM photograph) of 100 times magnification rate is transferred on tracing paper to obtain the $S_1$, the $S_2$ being obtained as the total area excluding the $S_1$. From these values, the ratio thereof can be obtained.

The present scintillator material consisting of the sintered body of rare earth oxysulfide phosphor such as mentioned above can be obtained by applying the following manufacturing methods for instance. In manufacturing the present ceramic scintillator material (sintered body), a HIP process is employed for instance. The texture where the coarse grains and fine grains are intermixed such as shown in FIG. 1B can be a transitional state in the growth process of grains. Accordingly, conditions in the process of HIP are important to be controlled.

First, a prescribed amount of compounds of each rare earth element such as Gd, Pr is measured, followed by sufficient mixing. In this case, for each starting material, an oxide such as for instance gadolinium oxide and praseodymium oxide can be used. For a mixture of the respective starting materials, it is preferable to use a homogeneous mixed oxide such as described in the following. That is, the respective rare earth oxides are dissolved in nitric acid, followed by coprecipitation by use of oxalic acid. The co-precipitated mixture substance including the respective rare earth elements is fired at a temperature of 900 to 1000° C. to obtain a homogeneous mixed oxide.

Then, to powder of the aforementioned mixed oxide of the rare earth elements, that is, to $Gd_2O_3$ powder including $Pr_2O_3$ of for instance $5 \times 10^{-2}$ mol, sulfurizing agent such as sulfur (S) and flux such as $A_3PO_4$ and $A_2CO_3$ (A denotes at least one kind selected from Li, Na, K, Rb and Cs) are thoroughly mixed. Such powder mixture is fired at a temperature of 1100 to 1300° C. for 5 to 10 hours, followed by washing with acid and water to obtain rare earth oxysulfide phosphor powder.

Thus obtained rare earth oxysulfide powder is used as raw material of phosphor ceramics (sintered body). The rare earth oxysulfide powder being used is preferable to have an average particle diameter in the range of 2 to 20 $\mu$m. When the average particle diameter of the rare earth oxysulfide powder is less than 2 µm, in molding by use of for instance cold isostatic press, the packing density becomes lower. As a result, in a subsequent HIP process for carrying out high temperature compression, a contraction becomes large. Accordingly, due to an increase of the contraction, the metal capsule is liable to be damaged. On the other hand, when the average particle diameter of the rare earth oxysulfide powder exceeds 20 µm, in the course of HIP process, a higher temperature is required to tend to deteriorate the strength, sensitivity and sensitivity distribution. The average particle diameter of the rare earth oxysulfide powder is more preferable to be in the range of 3 to 10 µm.

The rare earth oxysulfide powder such as mentioned above, after molding into an appropriate shape by use of a cold isostatic press, is packed in a metal capsule and sealed, the HIP process is carried out. Conditions in the course of HIP process are particularly important in the present invention. That is, a HIP temperature is preferable to be in the range of 1400 to 1600° C. When the HIP temperature is lower than 1400° C., the grain growth can not be sufficiently promoted. On the other hand, when the HIP temperature exceeds 1600° C., the grain growth proceeds rapidly to be difficult to obtain the intermixed texture that is characteristic to the present invention. Accordingly, more preferable HIP temperature is in the range of 1450 to 1550° C.

A HIP pressure is set at 98 MPa or more. When the HIP pressure is less than 98 MPa, a sufficient HIP effect can not be obtained. A HIP time, though depending on the HIP temperature and HIP pressure, when the HIP temperature is 1400 to 1600° C. and the HIP pressure is more than 98 MPa, is preferable to be in the range of 5 to 7 hours. By carrying out the HIP process to the rare earth oxysulfide powder under such conditions, the sintered texture can be controlled to be one in which the coarse grains of irregular polyhedron and the slender fine grains are intermixed. That is, the present scintillator material can be obtained with good reproducibility.

When the HIP temperature is lower than the aforementioned temperature or the HIP time is shorter than the aforementioned time, a sintered body having an agglomerate structure of primary particles such as shown in FIG. 1A is liable to be formed. Further, when the HIP temperature exceeds the aforementioned temperature and the HIP time is longer than the aforementioned time, a sintered body in which grains grow in random irregular polyhedrons such as shown in FIG. 1C is liable to occur.

According to a manufacturing process of a sintered body where the aforementioned HIP process is applied, a high-density sintered body of the rare earth oxysulfide phosphor can be obtained. When employing such sintered body as a ceramic scintillator, a scintillator slab of disc or rectangular plate is cut out of the sintered body. A shape of the scintillator slab, for a disc for instance, can be a diameter of 20 mm or more and a thickness of 0.5 mm or more, and for a rectangular plate, can be a length of short axis of 20 mm or more, that of long axis of 110 to 500 mm, and a thickness of 0.5 mm or more. When the thickness of a scintillator slab is less than 0.5 mm, stopping power of the X-rays and the strength of the scintillator chip subsequently prepared become insufficient. The preferable thickness is 1 mm or more. In order to cope with a demand for a longer length of the scintillator chip subsequently prepared, the diameter of the disc scintillator slab is preferable to be 90 mm or more. It is more preferable to be 300 mm or more. The length of short axis of the rectangular plate scintillator slab is, also from the identical reason, preferable to be 90 mm or more, more preferable to be 300 mm or more.

Since the sintered body of the rare earth oxysulfide phosphor due to the present invention is high in strength and excellent in uniformity, even such a large scintillator slab as mentioned above can be obtained with stability. Further, characteristics thereof can be excellently maintained and fluctuation of the characteristics can be largely lowered.

Further, by processing the scintillator slab such as mentioned above, scintillator chips of rectangular rod can be manufactured. The scintillator chips are used in a radiation detector as solid state scintillator. A shape of the scintillator chip can be for instance a length of 20 mm or more, a width of 0.5 to 2 mm, and a thickness of 0.5 to 3 mm. Due to the high strength characteristic that the present sintered body of the rare earth oxysulfide phosphor has, even the scintillator chips of the aforementioned dimension can be obtained with high yield. That is, in processing into scintillator chips of a length of 20 mm or more, even of 90 mm or more, still even of 300 mm or more, the scintillator slab can be largely suppressed from breaking and chipping. In particular, during the HIP process, the sintered body can be suppressed from cracking.

The present ceramic scintillator material is, as mentioned above, excellent in sensitivity characteristics and in a uniformity of the sensitivity distribution. By using the scintillator chips having the aforementioned shape as luminescence generating means, the downsizing of the detector element, an improvement of detection sensitivity of radiation and a suppression of artifacts can be realized. This largely contributes in downsizing and making high resolution a radiation detector.

The scintillator chip, in order to cope with an increase in the number of segments per one channel of a radiation detector, is demanded to be longer than ever. According to the present ceramic scintillator material, a scintillator chip of a length in the range of for instance 40 mm or more, 90 mm or more, 300 mm or more can be realized. A scintillator chip therein the present material like this is applied has such a high strength that bending strength measured by three point bending test method is 80 MPa or more.

According to the aforementioned scintillator of longer length, with a plurality of segments cut out of one chip one channel can be constituted. That is, the characteristics of the respective channels of a radiation detector can be made uniform. For instance, in an X-CT apparatus of multi-section tomography, one channel is constituted of lots of segments. The present scintillator chips are suitable for such applications.

Next, modes for implementing the present radiation detector and radiation inspection apparatus will be explained with reference to FIGS. 4, 5 and 6.

Figure 4:
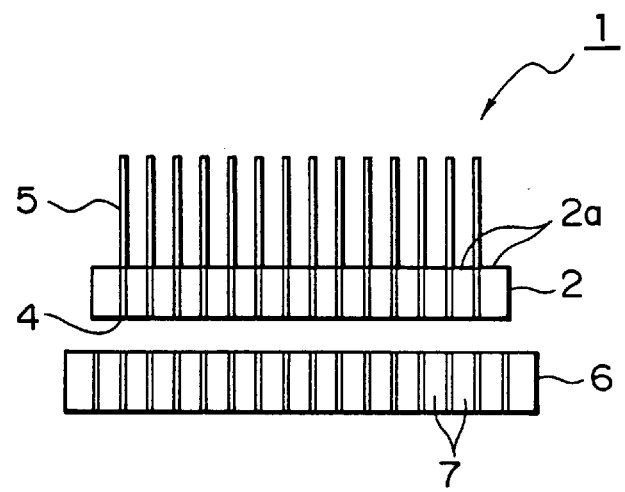
FIG. 4 is a diagram showing a schematic configuration of an X-ray detector as one embodiment of the present radiation detector.
Figure 5:
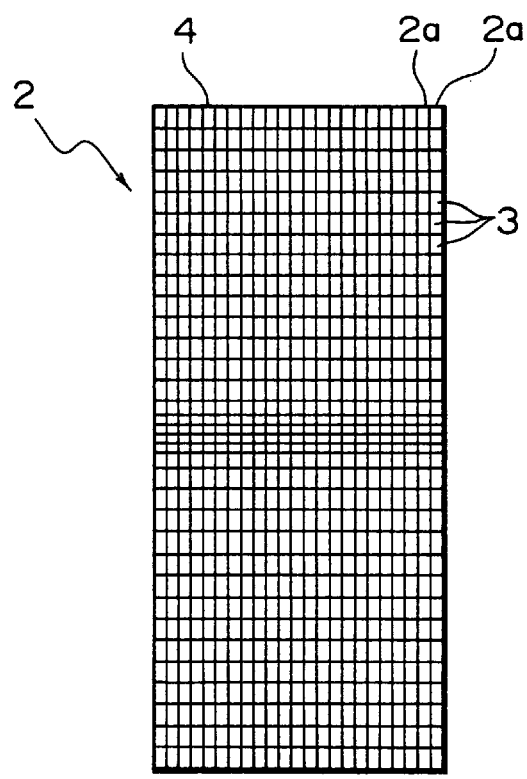
FIG. 5 is a diagram showing a scintillator block used in the X-ray detector shown in FIG. 4.

FIG. 4 shows a schematic configuration of one embodiment of an X-ray detector therein the present invention is applied. An X-ray detector 1 shown in the same figure comprises a scintillator block 2 as luminescence generating means. The scintillator block 2, as shown in FIG. 5, is constituted by integrating lots of segments 3 cut out of the aforementioned scintillator chip of the present invention lengthwise and breadthwise.

In the scintillator block 2, for each channel 2a, 2a, - - - , a plurality of segments 3 cut out of one piece of scintillator chip are used. By arranging the plurality of segments 3 cut out of one piece of scintillator chip in a lengthwise direction, the respective channels 2a, 2a, - - - are constituted. In the scintillator block 2, between the respective channels 2a, 2a, - - - , light-reflective material layers 4 are intervened.

In front of the respective channels 2a, 2a, - - - of the scintillator block 2, collimator plates 5 are disposed to restrict an incident direction of X-rays, thereby intersecting X-rays incident from an oblique direction to introduce only X-rays incident perpendicularly onto the scintillator block 2. The collimator plates 5 are disposed for the respective channels 2a, 2a, - - - to restrict an incident direction of X-rays. In the back of the scintillator block 2, a photoelectric conversion portion 6 is disposed. The photoelectric conversion portion 6 comprises a plurality of photodiodes 7 disposed corresponding to the respective segments 3, 3, - - - of the scintillator block 2.

In the aforementioned X-ray detector 1, X-rays enter in the scintillator block 2 and the respective segments 3 of the scintillator block 2 emit light according to an amount of the X-rays incident thereon. The light emitted from the respective segments 3 is detected by the respective corresponding photodiodes 7. That is, the light output emitted according to the incident amount of X-rays is converted into an electrical output through the photodiodes 7, thereby an amount of the incident X-rays being measured.

In the present X-ray detector 1 like this, since the channels 2a of the scintillator block 2 are constituted of a plurality of segments 3 cut out of the scintillator chip of the present invention, detection sensitivity of the X-rays can be improved and uniformity of the sensitivity (output) for each channel 2a, 2a, - - - can be increased. Therewith, characteristics and precision of the X-ray detector 1 can be largely improved. The X-ray detector 1 can be suitably used in an X-CT apparatus of multi-section tomography. In addition, such X-ray detectors can be manufactured with high precision and high yield.

Figure 6:
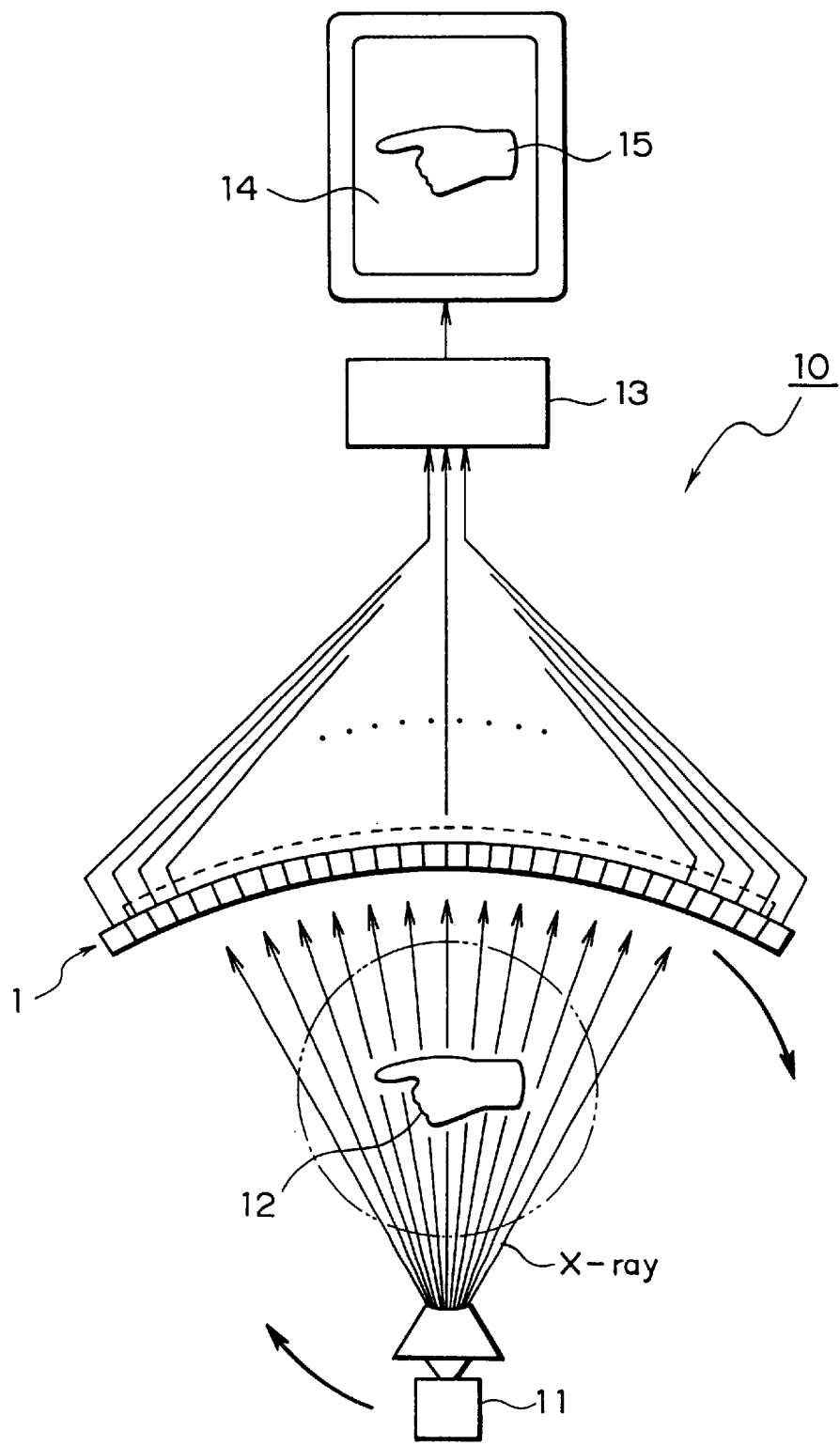
FIG. 6 is a diagram showing a schematic configuration of an X-CT apparatus as one embodiment of the present radiation inspection apparatus.

FIG. 6 is a diagram showing a schematic configuration of one embodiment of an X-CT apparatus therein the present invention is applied. An X-CT apparatus 10 shown in the same figure comprises the X-ray detector 1 of the aforementioned embodiment. The X-ray detectors 1 are stuck on a cylinder-like inner wall of an X-ray signal converting unit of the CT apparatus. At an approximate center of the arc thereto the X-ray detectors 1 are stuck, an X-ray tube 11 emitting X-rays is disposed. Between the X-ray detectors 1 and the X-ray tube 11, a fixed object 12 is disposed. The X-ray detector 1 and the X-ray tube 11 rotate together about the fixed object 12 as a center in the direction of an arcuate arrow, so that the X-ray detector 1 can pick up X-rays of varying intensities from different angles after transmission of the object 12. Thus, image information of the object 12 is three dimensionally collected from different angles.

A computer 13 processes signals obtained through the detector to show on a display 14 as an object image 15. The object image 15 is for instance a sectional radiograph of the object 15. In the X-CT apparatus of multi-section tomography, a plurality of sectional images of the object 12 are simultaneously taken. According to an X-CT apparatus of multi-section tomography like this, results of the imaging can be depicted three dimensionally.

In the X-CT apparatus 10 such as mentioned above, due to the use of the present scintillator chips excellent in uniformity of the sensitivity distribution, the artifacts (pseudo-image) can be effectively suppressed from appearing. Further, due to the high light output from the respective scintillators, resolution can be improved. With these, medical diagnosing capability due to the use of the X-CT apparatus 10 can be largely improved.

The present radiation inspection apparatus, without restricting to the X-ray inspection apparatus for medical diagnosis, can be applicable even to an X-ray nondestructive inspection apparatus for industrial use. The present invention contributes in improving inspection precision due to an X-ray nondestructive inspection apparatus.

In the following, concrete embodiments of the present invention will be described.

Embodiment 1

First, $Gd_2O_2S$:Pr (Pr concentration is 0.05 mol %) phosphor powder of an average particle diameter of 6 $\mu$m is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1500° C. and a period of 5 hours. Thus, a cylindrical sintered body (phosphor ceramics) of a diameter of approximately 80 mm×height of approximately 120 mm is manufactured. The sintered body is provided for the evaluation of the characteristics that will be described later.

Embodiment 2

$Gd_2O_2S$:Pr (Pr concentration is 0.05 mol %) phosphor powder of an average particle diameter of 10 $\mu$m is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1550° C. and a period of time of 5 hours. Thus, a sintered body (phosphor ceramics) of approximately similar shape with that of Embodiment 1 is manufactured. The sintered body is provided for the evaluation of the characteristics that will be described later.

Embodiment 3

$Gd_2O_2S$:Pr (Pr concentration is 0.05 mol %) phosphor powder of an average particle diameter of 3 $\mu$m is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1400° C. and a period of time of 6 hours. Thus, a sintered body (phosphor ceramics) of approximately similar shape with that of Embodiment 1 is manufactured. The sintered body is provided for the evaluation of the characteristics that will be described later.

Embodiment 4

$Gd_2O_2S$:Pr (Pr concentration is 0.05 mol %) phosphor powder of an average particle diameter of 12 $\mu$m is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1580° C. and a time period of 7 hours. Thus, a sintered body (phosphor ceramics) of approximately similar shape with that of Embodiment 1 is manufactured. The sintered body is provided for the evaluation of the characteristics that will be described later.

Embodiment 5

$Gd_2O_2S$:Pr (Pr concentration is 0.05 mol %) phosphor powder of an average particle diameter of 20 $\mu$m is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1600° C. and a time period of 6 hours. Thus, a sintered body (phosphor ceramics) of approximately similar shape with that of Embodiment 1 is manufactured. The sintered body is provided for the evaluation of the characteristics that will be described later.

Embodiment 6

(Gd$_{0.9}$La$_{0.1}$)$_2$O$_2$S:Pr (Pr concentration is 0.05 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1500° C. and a time period of 5 hours. Thus, a sintered body (phosphor ceramics) of approximately similar shape with that of Embodiment 1 is manufactured. The sintered body is provided for the evaluation of the characteristics that will be described later.

Embodiment 7

(Gd$_{0.9}$Y$_{0.1}$)$_2$O$_2$S:Pr (Pr concentration is 0.05 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1500° C. and a time period of 5 hours. Thus, a sintered body (phosphor ceramics) of approximately similar shape with that of Embodiment 1 is manufactured. The sintered body is provided for the evaluation of the characteristics that will be described later.

Embodiment 8

(Gd$_{0.1}$Lu$_{0.1}$)$_2$O$_2$S:Pr (Pr concentration is 0.05 mol %) phosphor powder of an average particle diameter of 12 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1580° C. and a time period of 6 hours. Thus, a sintered body (phosphor ceramics) of approximately similar shape with that of Embodiment 1 is manufactured. The sintered body is provided for the evaluation of the characteristics that will be described later.

Embodiment 9

Gd$_2$O$_2$S:Pr, Ce (Pr concentration is 0.05 mol %, Ce concentration is 0.0005 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1500° C. and a time period of 5 hours. Thus, a sintered body (phosphor ceramics) of approximately similar shape with that of Embodiment 1 is manufactured. The sintered body is provided for the evaluation of the characteristics that will be described later.

Embodiment 10

Gd$_2$O$_2$S:Pr, Zr (Pr concentration is 0.05 mol %, Zr concentration is 0.02 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1550° C. and a time period of 5 hours. Thus, a sintered body (phosphor ceramics) of approximately similar shape with that of Embodiment 1 is manufactured. The sintered body is provided for the evaluation of the characteristics that will be described later.

Embodiment 11

Gd$_2$O$_2$S:Pr (Pr concentration is 0.1 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1500° C. and a time period of 5 hours. Thus, a sintered body (phosphor ceramics) of approximately similar shape with that of Embodiment 1 is manufactured. The sintered body is provided for the evaluation of the characteristics that will be described later.

Embodiment 12

Gd$_2$O$_2$S:Pr (Pr concentration is 0.2 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1500° C. and a time period of 5 hours. Thus, a sintered body (phosphor ceramics) of approximately similar shape with that of Embodiment 1 is manufactured. The sintered body is provided for the evaluation of the characteristics that will be described later.

COMPARATIVE EXAMPLE 1

Gd$_2$O$_2$S:Pr (Pr concentration is 0.05 mol %) phosphor powder of an average particle diameter of 6 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1250° C. and a time period of 5 hours. Thus, a sintered body (phosphor ceramics) of approximately similar shape with that of Embodiment 1 is manufactured. The sintered body is provided for the evaluation of the characteristics that will be described later.

COMPARATIVE EXAMPLE 2

Gd$_2$O$_2$S:Pr (Pr concentration is 0.05 mol %) phosphor powder of an average particle diameter of 30 μm is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1650° C. and a time period of 2 hours. Thus, a sintered body (phosphor ceramics) of approximately similar shape with that of Embodiment 1 is manufactured. The sintered body is provided for the evaluation of characteristics that will be described later.

COMPARATIVE EXAMPLE 3

To Gd$_2$O$_2$S:Pr (Pr concentration is 0.05 mol %) phosphor powder of an average particle diameter of 6 μm, LiF of 0.08 mass % is added as a sintering aide, followed by sufficient mixing. The mixture is molded by use of a cold isostatic press. The molded body, after sealing in a Ta capsule, is set in a HIP processing apparatus. After introducing Ar gas in the HIP processing apparatus as a pressurizing medium, the sealed body is processed under conditions of a pressure of 147 MPa, a temperature of 1300° C. and a time period of 3 hours. Thus, a sintered body (phosphor ceramics) of approximately similar shape with that of Embodiment 1 is manufactured. The sintered body is provided for evaluation of the characteristics that will be described later.

From each of the sintered bodies (phosphor ceramics) of the aforementioned embodiments 1 to 12 and comparative examples 1 to 3, a scintillator slab of rectangular plate of 1×80×30 mm is cut out. Then, from the each scintillator slab, scintillator chips of rectangular rod of 1×2×30 mm are cut out. Yield during processing into scintillator chips is evaluated. With these scintillator chips, in the following way, the characteristics are evaluated, respectively.

Figure 7A:
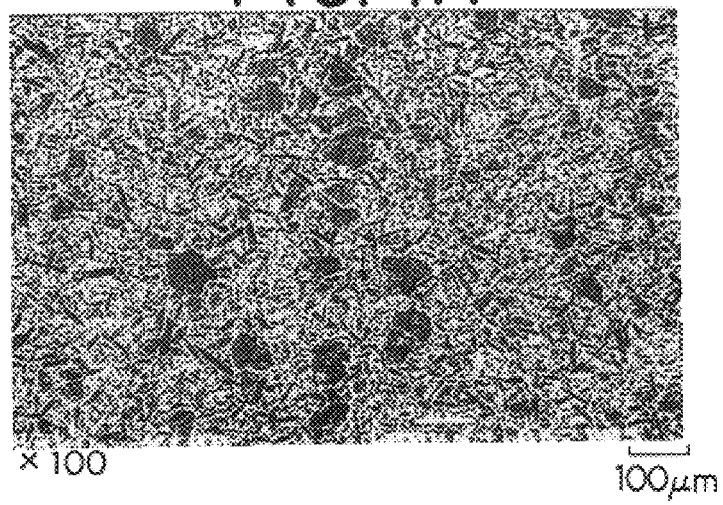
FIG. 7A, FIG. 7B and FIG. 7C are sectional photographs showing in enlargement the sintered texture of a ceramic scintillator material according to embodiment 1 of the present invention.
Figure 7B:
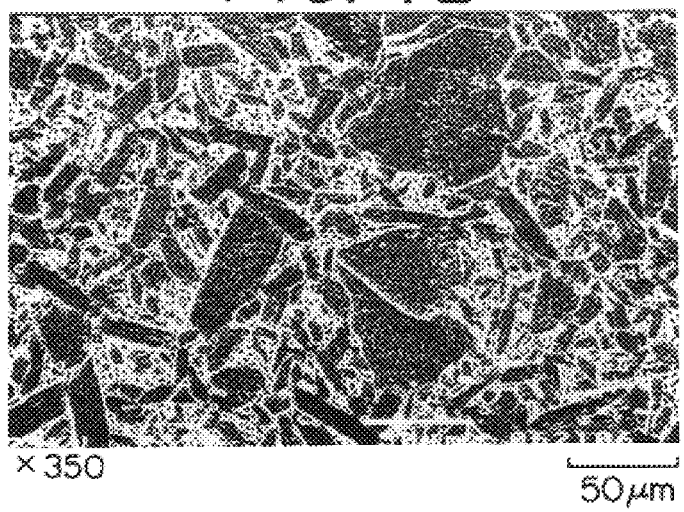
Figure 7C:
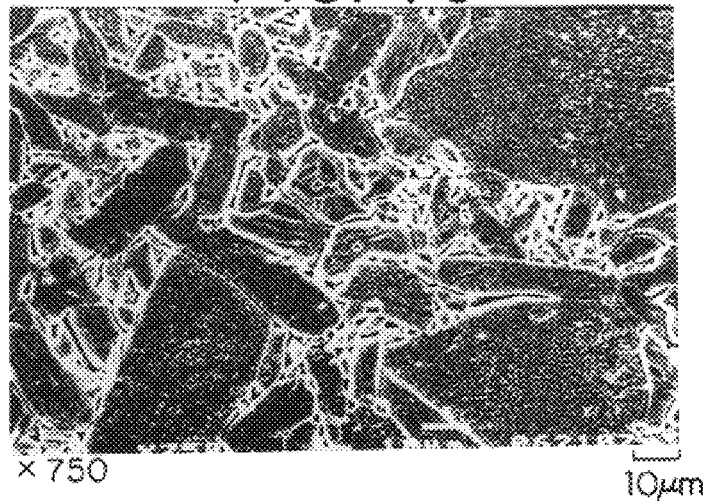

First, a cut surface of the each scintillator chip is lightly etched with inorganic acid or the like. The etched surface is observed with an electron microscope (SEM). FIGS. 7A, 7B and 7C are SEM photographs showing in enlargement the etched surfaces of the scintillator chips according to embodiment 1. FIG. 7B is a SEM photograph showing in further enlargement part of FIG. 7A, FIG. 7C being a SEM photograph showing in further enlargement part of FIG. 7B. From such SEM observations, a distribution of grain size is obtained. A concrete measurement method of grains is such as described earlier. Further, according to JIS R 1604 that defines three point bending test for evaluating bending strength of fine ceramics, the strength of the respective scintillator chips are measured. These results are shown in Table 1.

Next, X-rays (120 kVp, 300 mA) are irradiated on one of 1×30 mm surfaces of each scintillator chip to measure an electric current induced to a Si-photodiode disposed on the other 1×30 mm surface. This value of current denotes the sensitivity of the scintillator chip. In measuring the sensitivity distribution, X-rays, instead of being irradiated on the whole surface of the scintillator chip, are irradiated on the sample through a slit of a width of 1 mm while sequentially shifting the irradiating area from one end of the scintillator chip. From the respective current values, the sensitivity distribution along the chip length is obtained. As a reference for sensitivity measurement, a sample of $CdWO_4$ single crystal of the same dimension is cut to use. These results are shown in Table 1.

TABLE 1

| | Phosphor raw material | | | HIP conditions | | | Texture of sintered body | | | |
|---|---|---|---|---|---|---|---|---|---|---|
| | | | | | | | Coarse grain Average | Fine grain | | Area ratio |
| | Composition | Pr concentration (mol %) | Average particle diameter (μm) | Temperature (° C.) | Pressure (MPa) | Time (h) | size of coarse grain (μm) | Average short axis (μm) | Average long axis (μm) | of coarse grain to fine grain (%) |
| Embodiment 1 | $Gd_2O_2S:Pr$ | Pr: 0.05 | 6 | 1500 | 147 | 5 | 60 | 2 | 40 | 20 |
| Embodiment 2 | $Gd_2O_2S:Pr$ | Pr: 0.05 | 10 | 1550 | 147 | 5 | 80 | 3 | 50 | 40 |
| Embodiment 3 | $Gd_2O_2S:Pr$ | Pr: 0.05 | 2 | 1400 | 147 | 6 | 85 | 2 | 60 | 50 |
| Embodiment 4 | $Gd_2O_2S:Pr$ | Pr: 0.05 | 12 | 1580 | 147 | 7 | 50 | 5 | 50 | 40 |
| Embodiment 5 | $Gd_2O_2S:Pr$ | Pr: 0.05 | 20 | 1600 | 147 | 6 | 45 | 10 | 50 | 40 |
| Embodiment 6 | $(Gd, La)_2O_2S:Pr$ | Pr: 0.05 | 6 | 1500 | 147 | 5 | 70 | 3 | 50 | 30 |
| Embodiment 7 | $(Gd, Y)_2O_2S:Pr$ | Pr: 0.05 | 6 | 1500 | 147 | 5 | 50 | 2 | 40 | 20 |
| Embodiment 8 | $(Gd, Lu)_2O_2S:Pr$ | Pr: 0.05 | 12 | 1580 | 147 | 6 | 50 | 2 | 50 | 10 |
| Embodiment 9 | $Gd_2O_2S:Pr, Ce$ | Pr: 0.05 Ce: 0.0005 | 6 | 1500 | 147 | 5 | 50 | 2 | 40 | 20 |
| Embodiment 10 | $Gd_2O_2S:Pr, Zr$ | Pr: 0.05, Zr: 0.02 | 10 | 1500 | 147 | 5 | 80 | 5 | 50 | 50 |
| Embodiment 11 | $Gd_2O_2S:Pr$ | Pr: 0.1 | 6 | 1500 | 147 | 5 | 60 | 2 | 40 | 20 |
| Embodiment 12 | $Gd_2O_2S:Pr$ | Pr: 0.2 | 6 | 1500 | 147 | 5 | 60 | 2 | 40 | 20 |
| Comparative example 1 | $Gd_2O_2S:Pr$ | Pr: 0.05 | 6 | 1250 | 147 | 5 | — | 3 | 3 | 0 |
| Comparative example 2 | $Gd_2O_2S:Pr$ | Pr: 0.05 | 30 | 1650 | 147 | 2 | 80 | — | — | — |
| Comparative example 3 | $Gd_2O_2S:Pr*$ | Pr: 0.05 | 6 | 1300 | 100 | 3 | 10 | 10 | 30 | 55 |

| | Sensitivity (relative value) | Flucuation of sensitivity (%) | Strength (MPa) | Yield during 1 × 2 × 30 mm cutting (%) |
|---|---|---|---|---|
| Embodiment 1 | 165 | 0.5 | 113 | 93 |
| Embodiment 2 | 175 | 0.6 | 102 | 85 |
| Embodiment 3 | 170 | 0.8 | 98 | 83 |
| Embodiment 4 | 170 | 0.5 | 105 | 87 |
| Embodiment 5 | 165 | 0.7 | 88 | 81 |
| Embodiment 6 | 160 | 0.8 | 100 | 82 |
| Embodiment 7 | 180 | 0.9 | 95 | 80 |
| Embodiment 8 | 160 | 0.5 | 100 | 82 |
| Embodiment 9 | 110 | 0.2 | 122 | 100 |
| Embodiment 10 | 160 | 0.8 | 96 | 81 |
| Embodiment 11 | 160 | 0.5 | 113 | 92 |
| Embodiment 12 | 155 | 0.5 | 113 | 94 |
| Comparative | 120 | 0.8 | 60 | 47 |
| Comparative | 140 | 3.0 | 50 | 41 |
| Comparative example 3 | 135 | 0.5 | 75 | 55 |

*Sintering aide is used.

As shown in Table 1, all the scintillator chips consisting of the ceramic scintillator materials of the respective embodiments of the present invention have a texture in which coarse grains of irregular polyhedron and slender fine grains are intermixed. As obvious from FIGS. 7A, 7B and 7C, in the texture of the scintillator materials of the present invention, the slender fine grains fill voids in the surroundings of the coarse grains of irregular polyhedron. In the scintillator chips according to the respective embodiments, in a cut surface, the ratio of an area which the coarse grains occupy to an area which the fine grains occupy is in the range of 10:90 to 60:40. The scintillator chips consisting of the sintered body having such a fine texture are excellent in sensitivity characteristics and distribution thereof and have good mechanical strength.

On the other hand, in comparative example 1 having an agglomerate texture of fine grains, the sensitivity is low and the strength is also poor. Comparative example 2 that has a texture consisting only of coarse grains of random irregular polyhedron is poor in the strength and a little bit lower in the sensitivity, and has a larger fluctuation in the sensitivity distribution. Comparative example 3 in which a sintering aide is used is poor in the sensitivity and strength.

Further, each of the sintered bodies according to embodiments 1 to 12 showed such high yield as 80 to 100% during processing to the scintillator chips of rectangular rod of 1×2×30 mm. On the other hand, in comparative examples 1 to 3, all the yields are less than 60%, resulting in incapability of practical use. Thus, the present ceramic scintillator materials can cope with manufacture of longer size scintillator chips.

Embodiments 13, 14

From each of the sintered bodies manufactured identically with Embodiment 1 and 9, first, a scintillator slab of rectangular plate is cut out. Then, from each scintillator slab, scintillator chips of rectangular rod of 0.5×0.5×100 mm are cut out. The yields during processing into the scintillator chips are evaluated. These results are shown in Table 2.

COMPARATIVE EXAMPLES 4, 5

From each of the sintered bodies manufactured identically with Comparative Examples 1 and 3, first, a scintillator slab of rectangular plate is cut out. Then, from each scintillator slab, scintillator chips of rectangular rod of 0.5×0.5×100 mm are cut out. The yields when processing into the scintillator chips are evaluated. These results are shown in Table 2.

TABLE 2

|  | Yield during cutting out chips (0.5 × 0.5 × 100 mm) of rectangular rod | |
| --- | --- | --- |
| Embodiment 13 | Manufacturing method is same with Embodiment 1 | 83% |
| Embodiment 14 | Manufacturing method is same with Embodiment 9 | 92% |
| Comparative Example 4 | Manufacturing method is same with Comparative Example 1 | 0% |
| Comparative Example 5 | Manufacturing method is same with Comparative Example 3 | 5% |

As obvious from Table 2, according to the sintered bodies due to the present invention (ceramic scintillator material), even when processing to longer scintillator chips such as 0.5×0.5×100 mm, higher yield can be obtained. Even in processing into scintillator chips of a length of 330 mm, similar effects can be obtained. Thus, the present ceramic scintillator material can sufficiently cope with a demand of longer scintillator chips.

As obvious from the above, the present ceramic scintillator material, in addition to excellent light output (sensitivity characteristic), has the mechanical strength capable of coping with for instance the downsizing of a detector, and is excellent further in uniformity of the sensitivity distribution. According to the present radiation detector and radiation inspection apparatus using such ceramic scintillator material, resolution and imaging accuracy can be improved.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A ceramic scintillator material comprising a sintered body of a rare earth oxysulfide phosphor containing prasedymium as a primary activator;

wherein the sintered body comprises a texture where coarse grains of irregular polyhedron and slender fine grains are intermixed, and wherein the coarse grains have an average dimension in the range of 50 to 100 $\mu$m, and the fine grains have an average short axis in the range at 2 to 5 $\mu$m and an average long axis in the range of 5 to 100 $\mu$m.

2. The ceramic scintillator material as set forth in claim 1:

wherein in a section of a sintered body, a ratio of an area occupied by the coarse grains to an area occupied by the fine grains is in the range of 10:90 to 60:40.

3. The ceramic scintillator material as set forth in claim 1:

wherein the rare earth oxysulfide phosphor has a composition substantially expressed by a general formula:

$$RE_2O_2S:Pr$$

wherein RE denotes at least one element selected from the group consisting of Y, Gd, La and Lu.

4. The ceramic scintillator material as set forth in claim 3:

wherein the rare earth oxysulfide phosphor further contains at least one element selected from the group consisting of Ce, Zr and P as a coactivator.

5. The ceramic scintillator material as set forth in claim 1:

wherein the rare earth oxysulfide phosphor has a composition substantially expressed by a general formula:

$$(Gd_{1-x1}, RE'_{x})_2O_2S:Pr$$

wherein RE' denotes at least one element selected from the group consisting of Y, La and Lu, and x is a number satisfying $0 \leq x \leq 0.1$.

6. The ceramic scintillator material as set forth in claim 1:

wherein the ceramic scintillator material comprises a planar scintillator slab.

7. The ceramic scintillator material as set forth in claim 6:

wherein the scintillator slab is a disc having a diameter of 20 to 300 mm and a thickness of 0.5 to 1 mm.

8. The ceramic scintillator material as set forth in claim 6:

wherein the scintillator slab is a rectangular plate of a short side of 20 to 300 mm, a long side of 110 to 500 mm and a thickness of 0.5 to 1 mm.

9. The ceramic scintillator material as set forth in claim 1:

wherein the ceramic scintillator material comprises a scintillator chip of rectangular rod.

10. The ceramic scintillator material as set forth in claim 9:
wherein the scintillator chip has a shape of which length is 20 to 300 mm, width 0.5 to 2 mm, and thickness 0.5 to 3 mm.

11. A method for manufacturing a ceramic scintillator material comprising a rare earth oxysulfide phosphor containing praseodymium as a primary activator:
wherein a heat treatment condition and/or a pressure condition during manufacturing the sintered body is controlled so as to form an intermixed texture comprising coarse grains of irregular polyhedron having an average size of 50 to 100 μm and slender fine grains having an average short axis of 2 to 5 μm and an average long axis of 5 to 100 μm.

12. The method for manufacturing a ceramic scintillator material as set forth in claim 11, comprising:
a step of manufacturing the sintered body due to HIP procedure;
wherein as the heat treatment condition and/or the pressure condition, conditions of the HIP procedure are controlled.

13. A radiation detector, comprising:
a ceramic scintillator material as set forth in claim 1;
luminescence generating means for causing the ceramic scintillator material to generate light according to incident radiation; and
means for, after receiving the light generated from the luminescence generating means, carrying out photoelectric conversion of the light to an electric output.

14. The radiation detector as set forth in claim 13:
wherein the luminescence generating means is a radiation detector comprising a scintillator block where multiple scintillator segments manufactured by slicing a scintillator chip consisting of the ceramic scintillator material are integrated lengthwise and breadthwise.

15. The radiation detector as set forth in claim 14:
wherein the luminescence generating means comprises a plurality of respective channels, the respective channels having a configuration in which a plurality of segments manufactured by slicing the scintillator chip are integrated in a direction approximately perpendicular to a direction of arrangement of the plurality of channels.

16. A radiation inspection apparatus, comprising:
a radiation source for illuminating radiation toward an object to be inspected; and a radiation detector set forth in claim 15 for detecting radiation transmitted through the object.

17. The radiation inspection apparatus as set forth in claim 16:
wherein the radiation inspection apparatus is an X-ray tomograph.

* * * * *